United States Patent [19]
Verrett

[11] Patent Number: 5,998,663
[45] Date of Patent: *Dec. 7, 1999

[54] GRANULAR ALKALI METAL NITRILOTRIACETATE

[75] Inventor: Sheldon P. Verrett, Olivette, Mo.

[73] Assignee: Solutia, Inc., St. Louis, Mo.

[ * ] Notice: This patent issued on a continued prosecution application filed under 37 CFR 1.53(d), and is subject to the twenty year patent term provisions of 35 U.S.C. 154(a)(2).

[21] Appl. No.: 09/006,642

[22] Filed: Jan. 14, 1998

Related U.S. Application Data

[62] Division of application No. 08/647,959, filed as application No. PCT/US94/13652, Dec. 1, 1994, Pat. No. 5,744,639, which is a continuation of application No. 08/162,685, Dec. 3, 1993, abandoned.

[51] Int. Cl.$^6$ .................................................. C07C 229/00
[52] U.S. Cl. ........................................... 562/572; 252/546
[58] Field of Search .............................. 562/572; 252/546

[56] References Cited

U.S. PATENT DOCUMENTS

| | | | |
|---|---|---|---|
| 3,546,123 | 12/1970 | Stahlheber et al. | 252/137 |
| 3,591,630 | 7/1971 | Shen et al. | 260/534 E |
| 3,629,329 | 12/1971 | Shen et al. | 260/534 E |
| 3,684,744 | 8/1972 | Shen et al. | 252/546 |
| 3,717,589 | 2/1973 | Feiler et al. | 252/523 |
| 3,901,831 | 8/1975 | Shen et al. | 252/527 |
| 4,517,109 | 5/1985 | Merkenich et al. | 252/135 |
| 4,726,908 | 2/1988 | Kruse et al. | 252/91 |
| 4,810,099 | 3/1989 | Langsetmo | 366/168 |

FOREIGN PATENT DOCUMENTS

488868A2   6/1992   European Pat. Off. .

*Primary Examiner*—Michael L. Shippen
*Attorney, Agent, or Firm*—Arnold, White & Durkee

[57] ABSTRACT

There is disclosed a process for preparing highly absorptive granular alkali metal nitrilotriacetate by contacting NTA powder with an aqueous alkali metal silicate solution. A granular product having a majority of the granules, by weight, in the −12 to +80 mesh size range, which have a density of at least about 0.60 g/cc and an absorptivity in the absorptivity test in the range of above 7 ml/100 g is produced by contacting alkali metal nitrilotriacetate with an alkali metal silicate solution, mixing the material to granulate it and then drying the granules. A granular product having a density of at least about 0.60 g/cc, fewer than 15% fine material and an absorptivity in the range of from about 7–20 ml/100 g is produced.

6 Claims, No Drawings

GRANULAR ALKALI METAL NITRILOTRIACETATE

This is a divisional of application Ser. No. 08/647,959 filed Jul. 22, 1996, now U.S. Pat. No. 5,744,639, which is the national phase of PCT Application No. PCT/US94/13652, filed Dec. 1, 1994 which is a continuation of U.S. application Ser. No. 08/162,685, filed Dec. 3, 1993, now abandoned.

This invention relates to processes for the preparation of granular alkali metal nitrilotriacetate and, in particular, to processes for preparing highly absorptive granular alkali metal nitrilotriacetate. The invention also relates to the highly absorptive, granular alkali metal nitrilotriacetate product.

BACKGROUND OF THE INVENTION

Water-soluble salts of nitrilotriacetic acid are desirable detergent builders in formulations without phosphate builders. The powder form of the material tends to cake and there is little absorptivity. Detergent builders which absorb liquids have become desirable in recent years as a formulating tool which allows surfactant to be incorporated into a detergent formulation by way of being absorbed into the builder component.

Few process are known for granulating alkali metal nitrilotriacetate (NTA) and none for increasing the absorptivity of NTA. One such process is described in U.S. Pat. No. 3,629,329. Previous attempts to granulate NTA were motivated by the desire to reduce the caking tendency of the product. For this purpose a reaction mixture of the acid precursor, an alkali metal carbonate and water was formed wherein molar ratio of NTA to the alkali metal content of the carbonate was present in the ratio from about 1:2 to about 1:20. Water was added in the range of from about 5% to about 35% based on the total weight of the mixture. After mixing the mixture was dried to about 8% by weight moisture. A similar process, employing nitrilotriacetic acid and NTA in a ratio of 1:2 to 1:10 is disclosed in U.S. Pat. No. 3,591,630.

A composite detergent granulated product containing from about 3% to about 20% NTA and an inorganic salt selected from the group consisting of sodium metasilicate, sodium carbonate, and sodium sulfate is disclosed in U.S. Pat. No. 3,901,831. In this process, aqueous NTA is added to an agitated bed of inorganic salt having an initial temperature of from about 300° C. to about 550° C. so as to cool the bed to below 300° C. The bed is then dehydrated at a temperature of about 120° C.

A process for producing granular products containing disodium nitrilotriacetate is described in U.S. Pat. No. 3,546,123 wherein various acids are employed to wet trisodium nitrilotriacetate followed by agglomeration of the moistened particles and then drying the agglomerated particles to produce a product having a particle size in the range of smaller than a 4 mesh screen and larger than an 80 mesh screen and a density of from about 0.4 g/cc to about 0.8 g/cc. While such material is easily blended with spray dried detergent formulations, modern detergent formulations have a different consistency calling for a builder having a narrower range of density, i.e., above about 0.7 g/cc to be compatible with the remainder of the materials which may not be spray dried.

While flowability is improved, the above noted processes provided compositions having a wide range of particle size and densities, some of which provide little real difference between the granulated material and the powder material. Further, there is now a need for a nitrilotriacetate having considerably higher surfactant absorptivity than was achievable with prior art processes.

There is therefore needed a convenient process for the production of granular NTA having a consistent density in the medium range, that is, from about 0.7 g/cc to about 0.81 g/cc. Because the powder form of NTA is practically non-absorptive (about 2 g/cc) there is a need to produce NTA having a greatly increased absorptivity capacity in the range of from about 6 to 7 times greater than is now commercially available.

BRIEF DESCRIPTION OF THE INVENTION

There has now been discovered a convenient process for the production of highly absorptive, granular NTA having a density of from about 0.70 g/cc to about 0.81 g/cc and absorptivity of surfactant in the range of from about 12 to 20 ml/100 g. This type of product is obtained conveniently by contacting NTA powder with a partially neutralizing amount of sulfuric acid by either (1) contacting the NTA in a single step with a an aqueous solution containing from about 35% to about 60%, by weight, sulfuric acid, mixing the wetted NTA providing an acid addition time/mixing time ratio in the range of above about 0.75 to about 1; or (2) contacting the NTA powder with sulfuric acid in two steps, first with an aqueous solution of dilute sulfuric acid and then contacting the NTA with concentrated acid;

and then drying the granules whereby a majority of the granules, by weight, are in the −12 to +80 mesh size range, which have a density of at least about 0.70 g/cc and an absorptivity in an absorptivity test in the range of above 12 ml/100 g.

Another convenient process for the production of this highly absorptive, granular NTA has also been discovered. The desired granular NTA is obtained conveniently by:

(1) contacting NTA powder with an aqueous alkali metal silicate solution;

(2) mixing the wetted NTA to form granules; and (3) drying the granules whereby a majority of the granules, by weight, are in the −12 to +80 mesh size range, have a density of at least about 0.60 g/cc and an absorptivity in the absorptivity test greater than 7 ml/100 g.

There has also been discovered a highly absorptive, granular NTA having a density of from about 0.60 g/cc to about 0.81 g/cc, and preferably from is about 0.7 g/cc to about 0.81 g/cc; an absorptivity of surfactant in the range of from about 7 ml/100 g to about 20 ml/100 g, and preferably in the range of from about 12 ml/100 g to 18 ml/100 g; and a particle size distribution wherein a majority of the granules are within a range of from −12 to +80 U.S. mesh size.

DETAILED DESCRIPTION OF THE INVENTION

As defined above, NTA shall mean the alkali metal salt of nitrilotriacetic acid. Trisodium nitrilotriacetate monohydrate, sold commercially in powder form by Monsanto Company, is the preferred alkali metal salt of nitrilotriacetic acid, but other alkali metal salts of nitrilotriacetic acid may be used.

It has been found that when employing an aqueous solution of sulfuric acid having a concentration in the range of from about 35% to about 60% there is a critical ratio between the amount of time taken to add the acid and the amount of mixing time to achieve granulation in order to provide granules having the above described, desired properties of density, particle size distribution and absorptivity. This ratio has been found to be critical regardless of the shearing action in the mixing means to obtain the granules. The critical ratio, 0.75 to 1, relates the addition time during which the NTA is wetted and the total mixing time during which the partially neutralized material is granulated. It has been found that when mixing time is extended to ratios below about 0.75 either the absorptivity of the resulting granules is lowered below the desired range of from 12 to 14 ml/100 cc or the particle size distribution is unsatisfactory because the amount of fine material, that is, material which passes through an 80 mesh screen is excessive. It is desired to restrict the amount of such fine material to less than about 15%, by weight, of the total amount of granules produced. It has been found that an acid addition time/mixing time ratio of about 0.8 provides excellent results in the single step addition embodiment of this invention.

In the two-step method of adding the sulfuric acid, wherein a portion is added in the dilute aqueous form and the remainder in concentrated form, it has been found that the addition time/mixing time ratio is relaxed such that ratios as low as 0.15 can be employed while still achieving the desired density, particle size distribution and the desired absorptivity of surfactant in the range of from about 12 to 14 ml/100 cc. It is critical in the two-step method that the dilute acid be added first followed by the remainder in concentrated form. The concentration of the dilute aqueous sulfuric acid employed in the two step method is typically in the range of from about 2% to about 25% while the concentrated acid is typically oleum above 90% and usually having a concentration of about 98%.

Treatment of NTA with an aqueous solution of sulfuric acid in accordance with this invention results in at least a partial neutralization of the NTA. In most instances the NTA will be neutralized to the disodium nitrilotriacetic acid.

The amount of acid added to the NTA is essentially the same whether the single or two-step procedure is followed. The mole ratio (total) of acid to NTA is typically in the range of from about 0.17 to about 0.3. More preferably, the total amount of acid added to the dry NTA is in the range of from about 0.03 moles to about 0.09 moles. In the two step procedure, the mole ratio amount of acid to NTA added in dilute form is typically in the range of from about 0.007 to about 0.05 and the amount added in the concentrated form is in the range of from about 0.02 mole to about 0.28 of acid per mole of NTA.

While this description is directed to the use of the preferred sulfuric acid in the process of this invention, other acids and combinations of acids may be used. Similarly, other materials such as, for example, aqueous alkali metal silicate solutions can be used to produce the granular alkali metal nitrilotriacetate.

It has been found that when employing an aqueous solution of an alkali metal silicate that the amount of time taken to mix the silicate and the NTA powder to achieve granulation of the NTA is important in order to provide granules having the above described, desired properties of density, particle size distribution and absorptivity. The mixing time has been found to be important regardless of the shearing action in the mixing means to obtain the granules. It is necessary to have sufficient time to mix the NTA and the silicate to evenly coat the NTA particles with the silicate. However, it has been found that when mixing time is extended, the forming NTA granules will become too dense and either the absorptivity of the resulting granules is lowered below the desired range of from 7 to 20 ml/100 g or the particle size distribution is unsatisfactory as the particles become too large. Large granules may be crushed, but this may create excessive amounts of fine material. It is desired to restrict the amount of such fine material to less than about 15%, by weight, of the total amount of granules produced.

The addition of the aqueous alkali metal silicate solution in accordance with this invention, unlike processes using acid, does not cause a partial neutralization of the NTA. The preferred alkali metal silicate is a liquid silicate, RU® Silicate ($SiO_2/Na_2O$ ratio=2.4) produced by PQ Corporation. Sodium is the preferred alkali metal for both the alkali metal nitrilotriacetate and the alkali metal silicate. However, other alkali metals may be used and aqueous sodium silicates other than the preferred RU® Silicate may also be used. The ratio of the alkali metal silicate to the NTA, by weight, is preferably within the range of from about 0.17 to about 0.40 and the ratio is more preferably within the range of from about 0.25 to about 0.35.

The mixing operation can take any form including high, low and non-shear methods. Mixing provides a uniform treatment of the NTA as well as initiating the formation of granules. It has been found that granulated NTA produced in accordance with this invention has low frangibility, high absorptivity and uniform density in the medium density range of at least about 0.7 g/cc. In addition, the product is free-flowing and exhibits minimum caking and dusting. These properties are highly desired if the granular product is to be accepted for use in the production of detergent formulations. Typical means for mixing the NTA with acid or silicates in accordance with this invention are commercially available blenders and mixers. In all embodiments of this invention the acid or the silicate solution is typically sprayed onto an agitated mass of NTA. Mixing in accordance with this invention may take place in a rotary dryer, drum or the like. Typical commercially available mixing apparatus are those manufactured by Stephan Machine Corporation, Columbus, Ohio; Marion Mixers, Marion, Iowa; OtBrien Industrial Equipment Co., Inc., San Francisco, Calif.; Bepex Corp., Minneapolis, Minn. (sold under the tradename TURBOFLEX, also described in U.S. Pat. No. 4,810,099) or the like.

The preferred particle sizes included in the granules of this invention are those passing through a 12 mesh screen and retained upon an 80 mesh screen. As noted above, it is preferred that less than about 15 of the granules pass through an 80 mesh screen. Particles which are larger than will pass through a 12 mesh screen may be ground to reduce their size to the desired range thereby increasing the efficiency of the process.

The drying operation may take any suitable form such as fluid bed, tray, rotary or other means typically employed to dry granules. The drying temperature employed is usually in the range of from about 50° C. to about 75° C. Each drying apparatus will affect the apparent bulk density, particle size distribution and surface absorptivity characteristics of the finished product, the granulated NTA. It was found that granular NTA produced using a vacuum drying system had a higher surface absorptivity and a lower bulk density than granular NTA produced using a fluid bed drying system.

When prepared in accordance with this invention the granular product is compatible with modern detergent formulations commonly known as concentrated detergents. A density of at least about 0.6 g/cc and preferably about 0.7 g/cc can be blended successfully with the more dense, concentrated detergent ingredient containing surfactant and other additives typically incorporated into heavy duty laundry detergents such as optical brighteners, antiredeposition agents, corrosion inhibitors, dyes and pigments. The granules of this invention may also be blended with other builders such as is carbonates, citrates, sulfates, silicates and zeolites.

EXAMPLES

Absorptivity Test

The absorptivity of granules produced by addition of sulfuric acid to NTA so as to partially neutralize the NTA or of granules produced by the addition of an aqueous alkali metal silicate to NTA was determined by the following procedure. Into a 400 ml beaker was placed 50 g of granules to be tested. A 25 ml buret was filled with a non-ionic liquid surfactant, a linear alcohol alkoxylate commercially available from BASF under the tradename Plurafac D25. In a drop-wise manner the surfactant was added to the beaker while stirring with a scoopula. Surfactant droplets must be mixed with the test granules until the granules are sufficiently "wet". This is determined by forming a trough in the wetted granules with the scoopula and no granules fall into the trough when the beaker is tapped on the side with the scoopula at a point ¼ distance from the bottom from a distance of approximately 4 inches away from the beaker. The amount of surfactant added to the granules at this point is read from the buret and the absorptivity calculated on the basis of ml/100 g of granules.

Unless otherwise indicated the percentage amounts indicated in the following examples are weight percent. The NTA powder used is trisodium nitrilotriacetate monohydrate sold commercially by Monsanto Company.

Example 1

An agglomerator of the type manufactured by O'Brien Industrial Equipment Co., Inc., which incorporates a falling curtain of recirculated granules onto which is sprayed sulfuric acid in two steps, was employed. A charge of 45.36 kg of NTA powder was placed into the agglomerator. First, 4.762 kg of a 5% sulfuric acid solution was sprayed onto the falling film of granules and then 4.309 kg of 98% sulfuric acid was sprayed onto the film for a total addition time of 30 minutes for both additions. The batch was then mixed for an additional 10 minutes for a ratio of addition time/mix time of 0.75. The agglomerated material was dried in a fluid bed dryer at 50° C. for 30 minutes. The mesh size and fraction percent of the total weight obtained appears in Table I below. The bulk density of the −12 mesh to +80 mesh portion was found to be 0.71 g/cc and the absorptivity as determined by the above described absorptivity test was found to be 14.1 ml/100 g. The flow rate was 121.1 ml/sec indicating that the granules did not cake after being subjected to a standard caking test in a glass container at 100% humidity for 48 hr.

TABLE I

| Mesh Size | Fraction % |
|---|---|
| +12 | 14.95 |
| +20 | 19.70 |
| +40 | 22.78 |
| +60 | 14.47 |

TABLE I-continued

| Mesh Size | Fraction % |
|---|---|
| +80 | 8.39 |
| +100 | 6.27 |
| +200 | 13.45 |

Excessive fine material was produced because the amount of acid added to the NTA powder was insufficient to adequately wet the material.

Example 2

Into a Stephan Machine Corporation UMC-5 mixer was placed 850.2 g of NTA powder. The blade speed of the mixer was set at 900 rpm. In a first step of acid addition, 105.1 g of 15% aqueous sulfuric acid was added to the tumbling mass. Then 45.1 g of 98% sulfuric acid was added with a total addition time of 30 seconds. The wetted material was mixed for a total of 2 minutes and then dried in a fluid bed dryer at 50° C. for 30 minutes. The acid addition/mix time ratio was 0.25. The resulting granules had the size distribution noted in Table II below. The −12 to +80 mesh portion of the granules had a density of 0.73 g/cc and an absorptivity of 14.2 ml/100 g.

TABLE II

| Mesh Size | Fraction % |
|---|---|
| +12 | 35.86 |
| +20 | 18.67 |
| +40 | 20.52 |
| +60 | 11.23 |
| +80 | 4.16 |
| +100 | 2.58 |
| +200 | 6.98 |

Example 3

Into a Stephan Machine Corporation UMC-5 mixer was placed 850.2 g of NTA powder. The blade speed was set at 900 rpm. In step one, the powder was wetted with 95.1 g of 5% sulfuric acid followed by step two in which 55.1 g of 98% sulfuric acid was added to the tumbling mass. The total addition time for both steps was 20 seconds. The mixer was run for a total time of 2 minutes providing an acid addition/mix time ratio of 0.15. The −12 to +80 mesh portion of the granules had a bulk density of 0.74 g/cc and a flow rate of 122.4 ml/sec. Absorptivity was measured by the above test to be 12–13 ml/100 g for the −12 to +80 mesh portion of the granules. The particle size distribution obtained in weight percent appears in Table III below.

TABLE III

| Mesh Size | Fraction % |
|---|---|
| +12 | 19.24 |
| +20 | 25.79 |
| +40 | 27.55 |
| +60 | 12.97 |
| +80 | 4.422 |
| +100 | 2.80 |
| +200 | 7.22 |

Example 4

To a Stephan Machine Corporation UMC-5 mixer there was added 850.3 g of NTA powder. The blade speed was set at 900 rpm. In addition step one 60.1 g of 98% sulfuric acid was added to the tumbling mass and then, in addition step two, 90.1 g of water was added. The time for the addition of the acid was 15 seconds and the time for addition of the water was 15 seconds. The total mixing time was 30 seconds. The acid addition/mix time ratio was 1. The material was dried in a drum dryer at 50° C. The product had a bulk density of 0.80 g/cc and absorptivity of 13–14 ml/100 cc. The particle size distribution obtained in weight percent is shown below in Table IV.

TABLE IV

| Mesh Size | Fraction % |
|---|---|
| +12 | 13.80 |
| +20 | 22.16 |
| +40 | 13.09 |
| +60 | 12.01 |
| +80 | 12.23 |
| +100 | 10.12 |
| +200 | 16.60 |

In this example over 26%, by weight, of the granules were in the size range of smaller than +80 mesh indicating an unfavorable result. In fact the particle size distribution is almost even throughout the range which is not desirable. The product of this example also indicated considerable caking tendency. Thus it is shown that acid addition in both steps is necessary to achieve desirable results in accordance with this invention.

Example 5

To a mixer produced by Marion Mixer there was added 22.68 kg of NTA powder. With the mixer running there was added, in a single step, 4.5 kg of 50% sulfuric acid over a period of 10 minutes. The material was then mixed for an additional 10 minutes, a total of 20 minutes, providing an acid addition/mix time ratio of 0.5. The granules were then dried in a fluid bed drier at a temperature of 50° C. The –12 to +80 mesh portion of the dried granules had a bulk density of 0.71 g/cc and absorptivity of 14 ml/100 cc according to the above described absorptivity test. The particle size distribution by weight is shown in Table V below.

TABLE V

| Mesh Size | Fraction % |
|---|---|
| +12 | 26.53 |
| +20 | 20.65 |
| +40 | 12.75 |
| +60 | 9.51 |
| +80 | 11.38 |
| +100 | 5.69 |
| +200 | 13.49 |

The amount of fines, the particles passing through the 80 mesh screen, produced in this example amounted to nearly 20%, by weight of the total production, indicating an excessive amount. This is attributed to the low acid addition/mix time ratio 0.5.

Example 6

To an agglomerator of the type manufactured by O'Brien Industrial Equipment Co., Inc., as described in Example 1, there is added 45.36 kg of NTA powder. In one step 9.07 kg of 50% sulfuric acid was added by spraying the falling curtain of powder. The addition time was 30 minutes and the total mixing time was 40 minutes providing an acid addition/ mix time ratio of 0.75. The granules were dried in a fluid bed drier at 50° C. The product had a bulk density of 0.71 g/cc and an absorptivity of 14.1 in the absorptivity test described above. The particle size distribution in weight percent of the product is shown below in Table VI.

TABLE VI

| Mesh Size | Fraction % |
|---|---|
| +12 | 4.73 |
| +20 | 22.79 |
| +40 | 36.35 |
| +60 | 16.88 |
| +80 | 5.55 |
| +100 | 4.03 |
| +200 | 9.67 |

Example 7

Into a mixer manufactured by Marion Mixer, there was added 22.68 kg of NTA powder. Over a period of 15 minutes 4.54 kg of 50% aqueous solution of sulfuric acid was added to the powder while being mixed. The total mixing time continued for 18 minutes for an acid addition/mix time ratio of 0.83. The granulated material was dried in a fluid bed dryer at 50° C. The particle size distribution in weight percent is shown in Table VII below. The dried granules in the –12 to +80 size range had a density of 0.71 g/cc and an absorptivity of 14.1 ml/100 g.

TABLE VII

| Mesh Size | Fraction % |
|---|---|
| +12 | 27.57 |
| +20 | 23.28 |
| +40 | 22.58 |
| +60 | 15.66 |
| +80 | 5.76 |
| +100 | 3.18 |
| +200 | 1.96 |

As shown by the data in Table VII, the particle size distribution indicated a very low amount of fine material.

Example 8

Into an agglomerator of the type manufactured by O'Brien Industrial Equipment Co., Inc., as described above, there was placed 45.36 kg of NTA powder. Onto the falling film of powder there was sprayed 6.8 kg of a 50% aqueous solution of sulfuric acid over a period of 20 minutes. The total mixing time in the agglomerator was 30 minutes for an acid addition/mix time ratio of 0.66. The agglomerated material was then dried in a fluid bed dryer at a temperature of 50° C. The particle size distribution in weight percent is shown below in Table VIII. The –12 to +80 fraction had a density of 0.70 g/cc and an absorptivity of 11.0.

TABLE VIII

| Mesh Size | Fraction % |
|---|---|
| +12 | 5.78 |
| +20 | 12.24 |
| +40 | 15.70 |
| +60 | 15.43 |

TABLE VIII-continued

| Mesh Size | Fraction % |
| --- | --- |
| +80 | 13.81 |
| +100 | 10.66 |
| +200 | 26.38 |

The above data indicated the criticality of the acid addition/mix time ratio in that the absorptivity fell below the desired 12–14 range and the amount of fines increased to over 35%, by weight of the total product.

Example 9

To an agglomerator of the type manufactured by O'Brien Industrial Equipment Co., Inc., as described above, was added 45.63 kg of NTA powder. Over a period of 30 minutes 9.07 kg of a 50% aqueous solution of sulfuric acid was sprayed onto the falling curtain of powder. The total mix time in the agglomerator was 40 minutes providing a acid addition/mix time of 0.75. The agglomerated product was dried in a fluid bed dryer at a temperature of 50° C. The particle size distribution in weight percent is shown in Table IX below. The density of the granules in the −12 to +80 size range was 0.71 g/cc and the absorptivity was 14.1 ml/100 g.

TABLE IX

| Mesh Size | Fraction % |
| --- | --- |
| +12 | 4.73 |
| +20 | 22.79 |
| +40 | 36.35 |
| +60 | 16.88 |
| +80 | 5.55 |
| +100 | 4.03 |
| +200 | 9.67 |

Although still acceptable, the amount of fines in the product increased to 13.7%.

Example 10

Into a Stephan Machine Corporation UMC-5 mixer was placed 821.13 g of NTA powder. In a single step 183.59 g of a 40% aqueous solution of sulfuric acid was sprayed on the churning powder over a period of 15 seconds. The blade speed of the mixer was set at 1500 rpm to provide a high shear condition and the total mixing time was 15 seconds providing an acid addition/mix time ratio of 1. The granules were dried in a fluid bed dryer for 20 minutes at 50° C. The density of the −12 to +80 fraction was 0.73 and the absorptivity was 14.4 ml/100 g. The particle size distribution of the dried granules is shown below in Table X.

TABLE X

| Mesh Size | Fraction % |
| --- | --- |
| +12 | 35.19 |
| +20 | 26.98 |
| +40 | 20.30 |
| +60 | 8.43 |
| +80 | 2.26 |
| +100 | 1.26 |
| +200 | 5.57 |

Example 11

A Stephan Machine Corporation UMC-5 mixer was employed and the blade speed was set at 900 rpm. A charge of 750.3 g of NTA powder was placed into the mixer. Then 250 g of RU® Silicate was added to the NTA powder during an addition time of 30 seconds. The batch was then mixed for an additional 30 seconds. The agglomerated or granulated material was dried in a fluid bed dryer at 60° C. for 30 minutes. The mesh size and fraction percent of the total weight obtained appears in Table XI below. The bulk density of the −12 mesh to +80 mesh portion of the granules was found to be 0.71 g/cc and the absorptivity as determined by the above described absorptivity test was found to be 7.0 ml/100 g. The flow rate was 130.6 ml/sec indicating that the granules did not cake after being subjected to a standard caking test in a glass container at 100% humidity for 48 hr.

TABLE XI

| Mesh Size | Fraction % |
| --- | --- |
| +12 | 20.4 |
| +20 | 34.7 |
| +40 | 29.7 |
| +60 | 12.9 |
| +80 | 1.4 |
| +100 | 0.3 |
| −100 | 0.6 |

Example 12

Into a Stephan Machine Corporation UMC-5 mixer was placed 800 g of NTA powder. The blade speed of the mixer was set at 900 rpm. Then 200 g of RU® Silicate was added to the tumbling mass during an addition time of 30 seconds. The wetted material was mixed for a total of 1 minute and then dried in a fluid bed dryer at 60° C. for 30 minutes. The resulting granules had the size distribution noted in Table XII below. The mesh portion of the granules between −12 and +80 U.S. mesh size had a density of 0.72 g/cc and an absorptivity of 3.4 ml/100 g.

TABLE XII

| Mesh Size | Fraction % |
| --- | --- |
| +12 | 16.9 |
| +20 | 30.1 |
| +40 | 19.7 |
| +60 | 15.7 |
| +80 | 8.1 |
| +100 | 3.9 |
| −100 | 5.6 |

Example 13

Into a Stephan Machine Corporation UMC-5 mixer was placed 850 g of NTA powder. The blade speed was set at 900 rpm. The powder was wetted with 150 g of aqueous alkali metal silicate solution, RU® Silicate, during an addition time of 30 seconds. The mixer was run for a total time of 1 minute. The granular material was dried in a vacuum drier overnight at a temperature of 60° C. The granules within the −12 to +80 U.S. mesh size had a bulk density of 0.63 g/cc and a flow rate of 64.6 ml/sec. Absorptivity was measured by the above test to be 10 ml/100 g. The particle size distribution obtained in weight percent appears in Table XIII below.

TABLE XIII

| Mesh Size | Fraction % |
| --- | --- |
| +12 | 20.2 |
| +20 | 28.3 |
| +40 | 27.3 |
| +60 | 17.5 |
| +80 | 4.7 |
| +100 | 1.2 |
| -100 | 0.9 |

Example 14

Into a Stephan Machine Corporation UMC-5 mixer there was added 800 g of NTA powder. The blade speed was set at 900 rpm. The powder was wetted by the addition of 200 g of an aqueous silicate solution, RU® Silicate. The time for the addition of the silicate was 30 seconds and the total mixing time was 1 minute. The granular material was dried in a vacuum dryer overnight at 60° C. The product had a bulk density of 0.59 g/cc and absorptivity of 16–20 ml/100 g. The particle flow rate was 95.9. The particle size distribution obtained in weight percent is shown below in Table XIV.

TABLE XIV

| Mesh Size | Fraction % |
| --- | --- |
| +12 | 20.2 |
| +20 | 28.3 |
| +40 | 27.3 |
| +60 | 17.5 |
| +80 | 4.7 |
| +100 | 1.2 |
| -100 | 0.9 |

Example 15

Into a Stephan Machine Corporation UMC-5 mixer there was added 1875 g of NTA powder. With the mixer running at 900 rpm, there was added 625 g of an aqueous alkali metal silicate solution, RU® Silicate, over a period of 30 seconds. The material was then mixed for an additional 30 seconds. The granules were then dried in a vacuum dryer overnight at a temperature of 60° C. The -12 to +80 mesh portion of the dried granules had a bulk density of 0.60 g/cc and absorptivity of 15–18 ml/100 g according to the above described absorptivity test. The particle size distribution by weight percent is shown in Table XV below.

TABLE XV

| Mesh Size | Fraction % |
| --- | --- |
| +12 | 14.4 |
| +20 | 43.4 |
| +40 | 19.9 |
| +60 | 10.2 |
| +80 | 4.1 |
| +100 | 5.5 |
| -100 | 2.5 |

Although the invention was described with respect to specific examples which are set forth in considerable detail, it should be understood that this is by way of illustration only and that the invention is not necessarily limited thereto since alternative embodiments and operating techniques will become apparent to those skilled in the art in view of the disclosure. Accordingly, modifications are contemplated which can be made without departing from the spirit of the described invention.

What is claimed is:

1. A granular alkali metal nitrilotriacetate (NTA) produced by the addition of an aqueous alkali metal silicate solution to powder NTA, wherein said granular NTA is composed of agglomerated NTA particles, the granular NTA having a density within the range of from about 0.6 g/cc to about 0.81 g/cc, an absorptivity in the absorptivity test greater than about 7 ml/100 g and a particulate size distribution in which a majority of the granules are within a range of from -12 to +60 U.S. mesh size.

2. The granular NTA of claim 1 wherein the absorptivity in the absorptivity test is greater than about 12 ml/100 g.

3. The granular NTA of claim 1 wherein the aqueous alkali metal silicate solution is a sodium silicate solution.

4. A granular alkali metal nitrilotriacetate (NTA) comprising granules said granules are composed of agglomerated NTA particles, wherein said NTA granules having a density within the range of from about 0.6 g/cc to about 0.81 g/cc, an absorptivity in the absorptivity test greater than about 7 ml/100 g and a particulate size distribution in which a majority of the granules are within a range of from -12 to +60 U.S. mesh size and wherein the granular NTA has a weight ratio of alkali metal silicate to NTA in the range from 0.17 to 0.40.

5. A granular alkali metal nitrilotriacetate (NTA) comprising granules said granules are composed of agglomerated NTA particles, wherein said NTA granules having a density within the range of from about 0.6 g/cc to about 0.81 g/cc, an absorptivity in the absorptivity test greater than about 7 ml/100 g and a particulate size distribution in which a majority of the granules are within a range of from -12 to +60 U.S. mesh size and wherein the granular NTA has a weight ratio of alkali metal silicate to NTA in the range from 0.25 to 0.35.

6. A granular alkali metal nitrilotriacetate (NTA), wherein said granular alkali metal nitrilotriacetate is the product of the process including: mixing powdered nitrilotriacetate with an aqueous alkali metal silicate solution so as to form granules of agglomerated nitrilotriacetate powder and drying said granules and wherein said granular alkali metal nitrilotriacetate has a particulate size distribution in which a majority of the granules are within a range of from -12 to +60 U.S. mesh size and wherein said granular alkali metal nitrilotriacetate has an absorbtivity in the absorbtivity test of at least about 7 ml/100 gm, and wherein said granular alkali metal nitrilotriacetate has a density within the range of from about 0.6 g/cc to about 0.81 g/cc and wherein said granular alkali metal nitrilotriacetate has a weight ratio of alkali metal silicate to NTA in the range from 0.17 to 0.40.

* * * * *

UNITED STATES PATENT AND TRADEMARK OFFICE
CERTIFICATE OF CORRECTION

PATENT NO. : 5,998,663
DATED : December 7, 1999
INVENTOR(S) : Sheldon P. Verrett It is certified that error appears in the above-identified patent and that said Letters Patent is hereby corrected as shown below:

In col. 4, Line 42, delete "OtBrien" and insert --O'Brien--.

Signed and Sealed this

Eleventh Day of July, 2000

*Attest:*

Q. TODD DICKINSON

*Attesting Officer*     *Director of Patents and Trademarks*